(12) United States Patent
Mirramezani et al.

(10) Patent No.: US 12,175,594 B2
(45) Date of Patent: Dec. 24, 2024

(54) REDUCED ORDER MODEL FOR COMPUTING BLOOD FLOW DYNAMICS

(71) Applicant: The Regents of the University of California, Oakland, CA (US)

(72) Inventors: Seyed Mehran Mirramezani, Albany, CA (US); Shawn Shadden, Albany, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 169 days.

(21) Appl. No.: 17/621,645

(22) PCT Filed: Jun. 26, 2020

(86) PCT No.: PCT/US2020/039765
§ 371 (c)(1),
(2) Date: Dec. 21, 2021

(87) PCT Pub. No.: WO2020/264259
PCT Pub. Date: Dec. 30, 2020

(65) Prior Publication Data
US 2022/0237864 A1    Jul. 28, 2022

Related U.S. Application Data

(60) Provisional application No. 62/867,041, filed on Jun. 26, 2019.

(51) Int. Cl.
*G06T 17/00* (2006.01)
*A61B 34/10* (2016.01)
(Continued)

(52) U.S. Cl.
CPC .............. *G06T 17/00* (2013.01); *A61B 34/10* (2016.02); *G06T 7/0012* (2013.01); *G06T 7/60* (2013.01);
(Continued)

(58) Field of Classification Search
CPC .................. A61B 34/10; G06T 17/00; G06T 2207/30048; G06T 2207/30104;
(Continued)

(56) References Cited

U.S. PATENT DOCUMENTS

2015/0324962 A1    11/2015  Itu et al.
2016/0070877 A1 *  3/2016  Taylor .................... A61B 5/029
                                            703/9
(Continued)

FOREIGN PATENT DOCUMENTS

WO    WO-2021064372 A1 *  4/2021  ........... G06T 7/0012

OTHER PUBLICATIONS

Use of mathematical modeling to study pressure regimes in normal and Fontan blood flow circulations, Mar. 6, 2019, Marina Chugunova (Year: 2019).*
(Continued)

*Primary Examiner* — Ming Wu
(74) *Attorney, Agent, or Firm* — McCoy Russell LLP

(57) ABSTRACT

A computer-implemented method can include generating centerlines of a patient's cardiovascular network, determining geometric features of the cardiovascular network based on the centerlines and a three-dimensional (3D) computer model of the cardiovascular network, constructing a lumped parameter network (LPN) of resistors corresponding to the cardiovascular network, and solving a system of equations corresponding to flow and pressure for the LPN model.

18 Claims, 13 Drawing Sheets

(51) Int. Cl.
  *G06T 7/00* (2017.01)
  *G06T 7/60* (2017.01)
(52) U.S. Cl.
  CPC ............... *A61B 2034/105* (2016.02); *G06T 2207/30048* (2013.01); *G06T 2207/30104* (2013.01); *G06T 2210/24* (2013.01); *G06T 2210/41* (2013.01)
(58) Field of Classification Search
  CPC ............ G06T 2210/24; G06T 2210/41; G06T 7/0012; G06T 7/60; G16H 30/40; G16H 50/20; G16H 50/50
  See application file for complete search history.

(56) References Cited

U.S. PATENT DOCUMENTS

| | | | |
|---|---|---|---|
| 2017/0004278 A1* | 1/2017 | Marsden | G06F 30/23 |
| 2017/0360351 A1* | 12/2017 | Unni | G06N 3/08 |
| 2018/0140258 A1 | 5/2018 | Fonte et al. | |

OTHER PUBLICATIONS

ISA United States Patent and Trademark Office, International Search Report and Written Opinion Issued in Application No. PCT/US2020/039765, Sep. 30, 2020, WIPO, 13 pages.

* cited by examiner

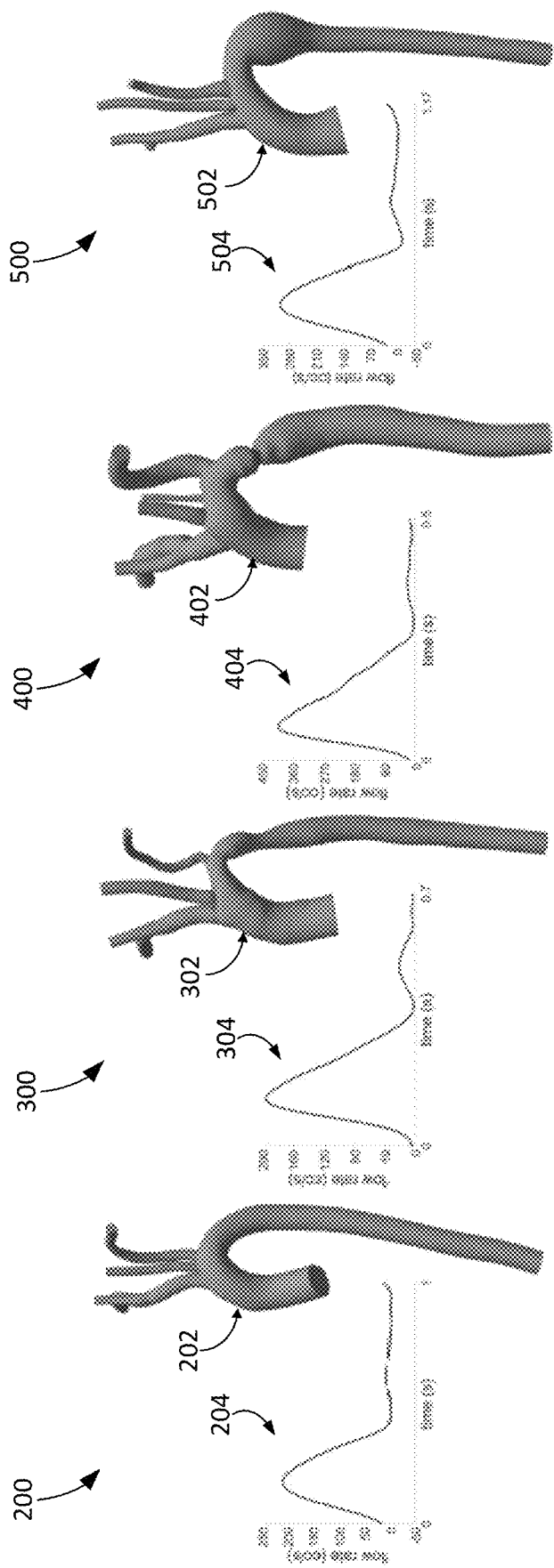

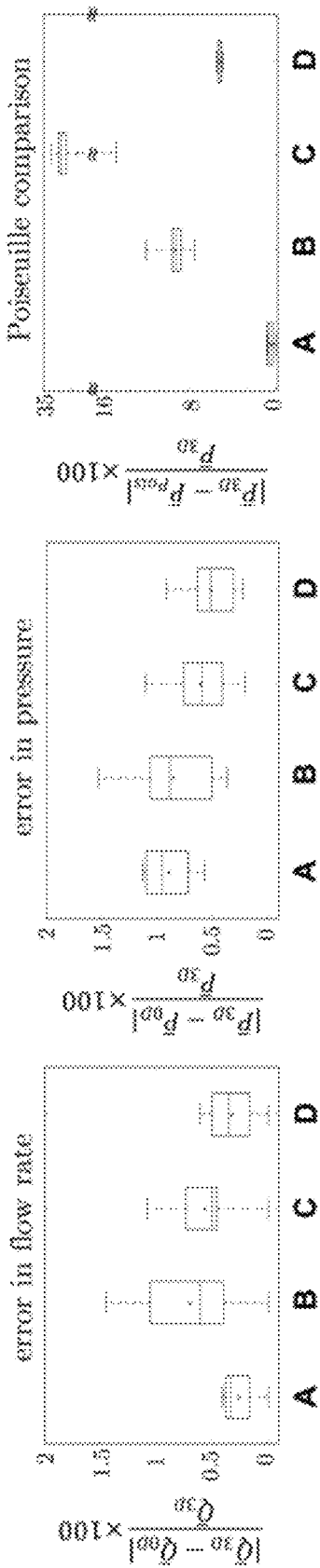

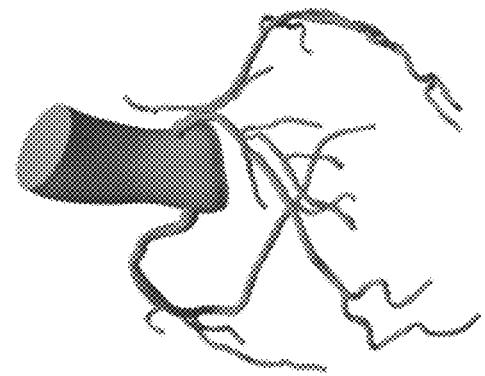
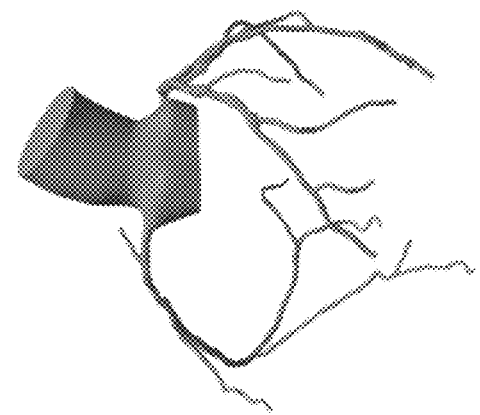
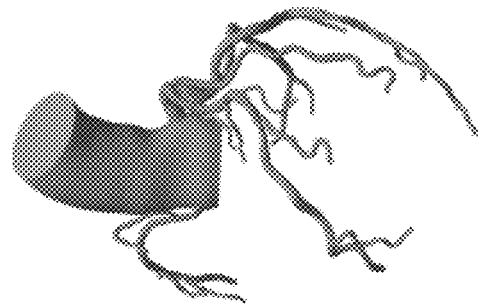
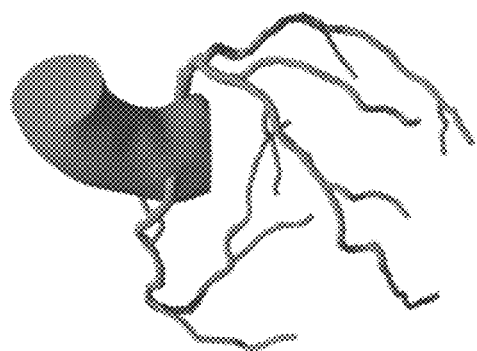
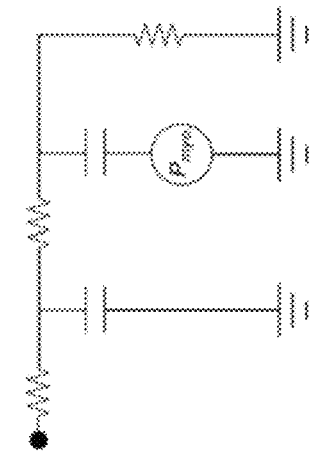
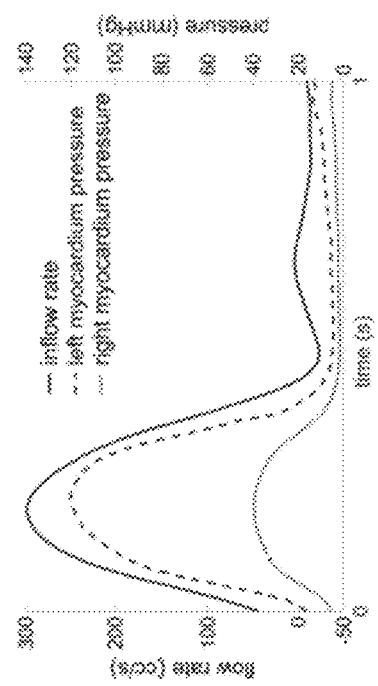

REDUCED ORDER MODEL FOR COMPUTING BLOOD FLOW DYNAMICS

CROSS-REFERENCE TO RELATED APPLICATIONS

The present application is a U.S. National Phase of International Patent Application No. PCT/US2020/039765, entitled "REDUCED ORDER MODEL FOR COMPUTING BLOOD FLOW DYNAMICS," filed on Jun. 26, 2020, which claims priority to U.S. Provisional Patent Application No. 62/867,041, entitled "REDUCED ORDER MODEL FOR COMPUTING BLOOD FLOW DYNAMICS," filed Jun. 26, 2019. The entire contents of each of the above-identified applications are hereby incorporated by reference for all purposes.

GOVERNMENT SUPPORT

This invention was made with government support under Grant Number HL103419 awarded by the National Institutes of Health. The government has certain rights in the invention.

BACKGROUND

Image-based computational fluid dynamics (CFD) is the current standard to study global and local blood flow features in the cardiovascular system. Applications of image-based CFD are numerous, and include assessment of pathologies, such as vascular stenosis, aneurysms, and dissection, as well as for surgical planning and the evaluation of medical devices. This technology has grown considerably over the last decade, gaining recent FDA approval and clinical adoption. Although image-based CFD enables comprehensive analysis of hemodynamics, it is computationally expensive, prone to numerical instabilities, and can be sensitive to numerical-method parameters. These factors have limited broader translation of image-based CFD to clinical settings, and have limited the ability to perform parametric analyses in cardiovascular applications such as uncertainty quantification, sensitivity analysis, data assimilation, optimization, parameter tuning, etc. Such ensemble-based studies are becoming crucial as hemodynamics modeling matures from a tool for exploratory research, to a paradigm for improving healthcare decisions. These factors motivate the need for reduced-order models (ROMs) of blood flow to be used in place of or in conjunction with fully-resolved CFD modeling.

ROMs can roughly be divided into data-fitting methods (e.g. polynomial chaos expansion, machine learning, etc.) and theory-based methods. The main focus here is on theory-based methods. The most basic ROMs are lumped parameter network (LPN) models. Like the Navier-Stokes equation, LPNs describe a mathematical relationship between flow, pressure and their derivatives; however, the relationship is given by an ordinary differential equation (ODE) and algebraic equation (AE). Mostly, LPNs can be interpreted as electrical circuit analogs. The most basic example being a vascular network (or single vessel) modeled is a resistor, where flow rate is linearly proportional to pressure drop across the network (vessel). The 3-element "RCR" is a popular and simple LPN, but more elaborate LPNs are also widely employed. LPN models are generally used to describe complete vascular territories, and by construction, continuous spatial variations in flow and pressure are not resolved.

In order to resolve continuous spatial variations in flow and pressure, the most common reduced-order modeling approach is to cross-sectionally average the Navier-Stokes equations to generate 1D (or quasi-1D) equations. This approach has been used extensively for decades to understand vascular fluid dynamics. Similarly, 2D models have been proposed to generalize 1D models while still reducing the computational cost of CFD simulation. Both 1D and 2D models are described by partial differential equations (PDEs), and are thus more computationally expensive than LPN models and more prone to numerical artifacts and instability.

The basic idea of lumped parameter modeling can be used to develop quasi-distributed pressure-flow models. For example, in prior works blood flow through a network of cerebrovascular arteries was modeled by assigning a net viscous resistance to each segment in the model and coupled with expected pressure losses at bifurcations. The underlying assumptions of Poiseuille flow break down in larger arteries and veins and other sources of energy dissipation such as from flow unsteadiness, kinetic effects, and vessel curvature can be significant.

SUMMARY

Implementations of the disclosed technology are generally directed to methods and systems for non-invasive assessment of blood flow dynamics (hemodynamics) information based on features extracted from angiographic medical image data. The proposed techniques generally rely on principles of fluid mechanics to develop a subject-specific lumped parameter network (LPN) of resistors (a surrogate model) describing expected energy losses along vascular segments, including from viscous dissipation, unsteadiness, flow separation, vessel curvature and vessel bifurcations. The surrogate model incorporates additional LPNs or mathematical relations that can describe upstream or downstream physiologic effects. Compared to computational fluid dynamics (CFD) methods that have traditionally been used to compute hemodynamics data, this methodology presents a significant reduction in computational effort and complexity.

This approach could be used to rapidly compute blood flow or pressure information from medical images or image-based computer models. Relevant information could include prediction of pressure drop across stenotic vascular segments.

BRIEF DESCRIPTION OF THE DRAWINGS

FIG. 2 illustrates a first example 200 of an aorta model 202 that may be used in connection with implementations of the disclosed technology and corresponding time-varying inflow waveform 204.

FIG. 3 illustrates a second example 300 of an aorta model 302 that may be used in connection with implementations of the disclosed technology and corresponding time-varying inflow waveform 304.

FIG. 4 illustrates a third example 400 of an aorta model 402 that may be used in connection with implementations of the disclosed technology and corresponding time-varying inflow waveform 404.

FIG. 5 illustrates a fourth example 500 of an aorta model that may be used in connection with implementations of the disclosed technology and corresponding time-varying inflow waveform 504.

FIG. 6 illustrates an example 600 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlet of the aortic models 202, 302, 402, and 502 of FIGS. 2-5, respectively.

FIG. 7 illustrates an example 700 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlet of the aortic models 202, 302, 402, and 502 of FIGS. 2-5, respectively.

FIG. 8 illustrates an example 800 of mean pressure errors between the 3Dt CFD and a DLP model assigning a Poiseuille resistance to each vascular segment ($\overline{P}_{pois}$), of the aortic models 202, 302, 402, and 502 of FIGS. 2-5, respectively.

FIG. 16 illustrates a first example 1600 of a coronary model 1602 that may be used in connection with implementations of the disclosed technology 1604.

FIG. 17 illustrates a second example 1700 of a coronary model 1702 that may be used in connection with implementations of the disclosed technology.

FIG. 18 illustrates a third example 1800 of a coronary model 1802 that may be used in connection with implementations of the disclosed technology.

FIG. 19 illustrates a fourth example 1900 of a coronary model 1902 that may be used in connection with implementations of the disclosed technology.

FIG. 20 illustrates an example 2000 of a typical time-varying inflow waveform, left myocardium pressure waveform, and right myocardium pressure waveform prescribed at the ascending aorta of the models 1602, 1702, 1802, and 1902 of FIGS. 16-19, respectively.

DETAILED DESCRIPTION

Figure 1:
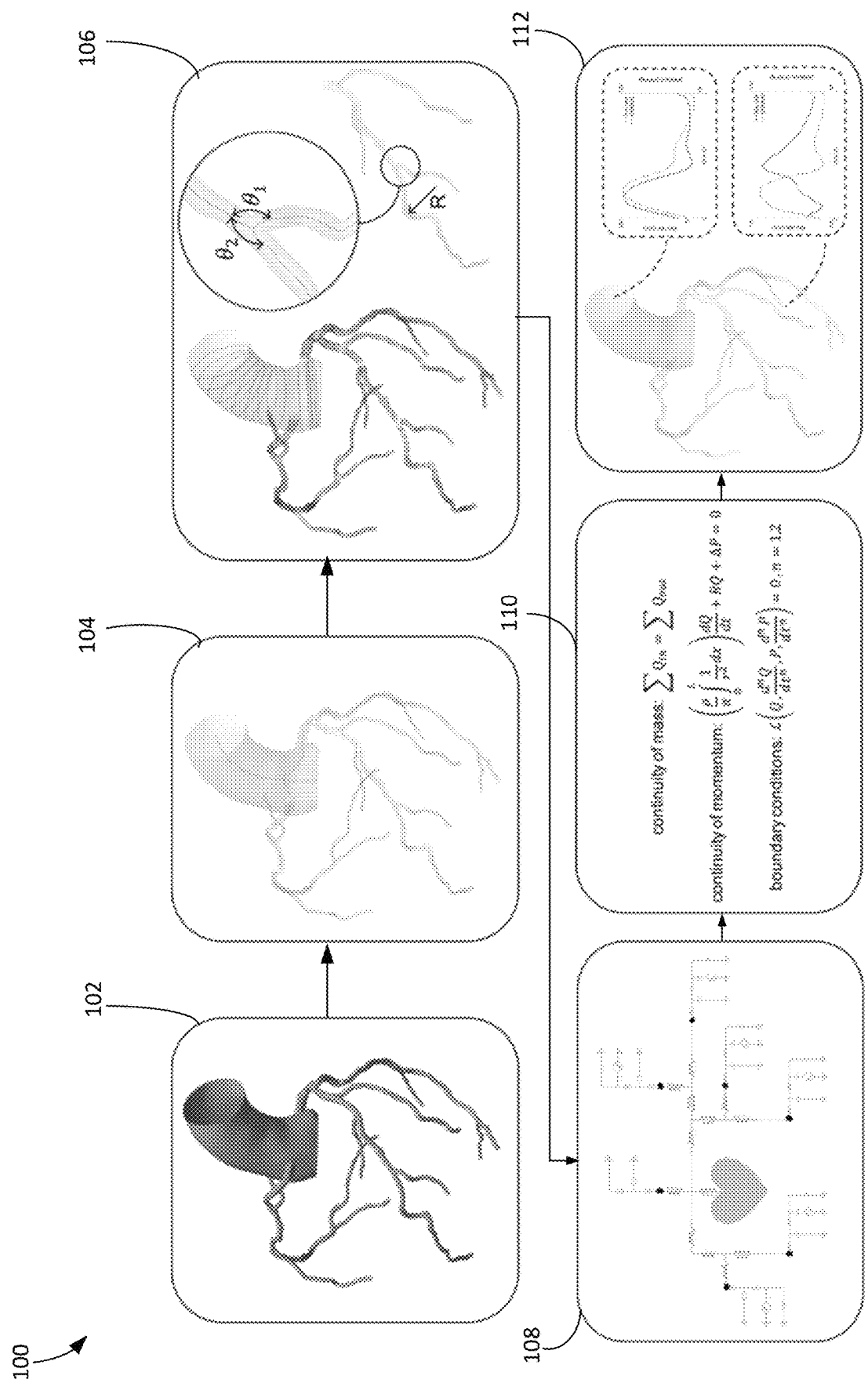
FIG. 1 illustrates an example of modeling steps of a framework 100 for computing blood flow and pressure in a representative patient-specific coronary model using a distributed LP method in accordance with the disclosed technology.
Figure 12:
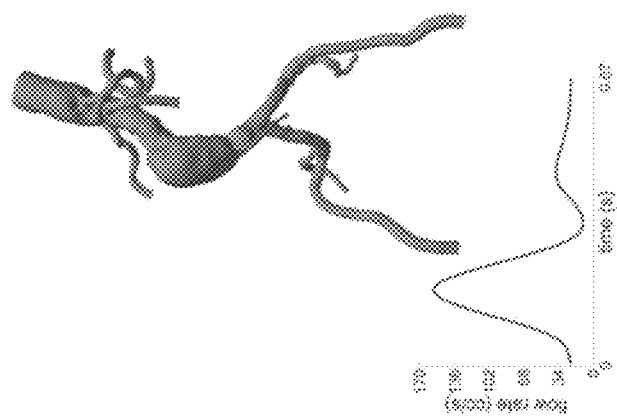
FIG. 12 illustrates a fourth example 1200 of an aorto-femoral model 1202 that may be used in connection with implementations of the disclosed technology and corresponding time-varying inflow waveform 1204.
Figure 11:
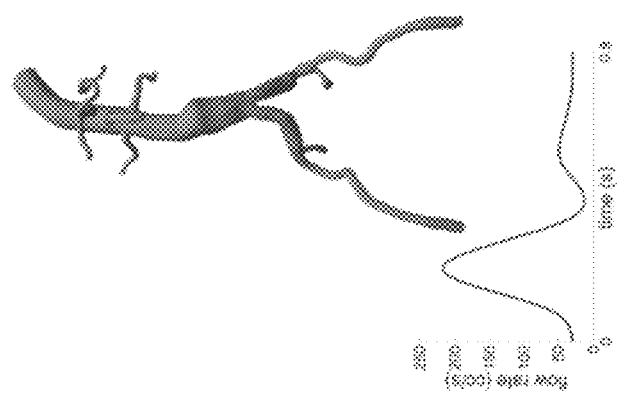
FIG. 11 illustrates a third example 1100 of an aorto-femoral model 1102 that may be used in connection with implementations of the disclosed technology and corresponding time-varying inflow waveform 1104.
Figure 10:
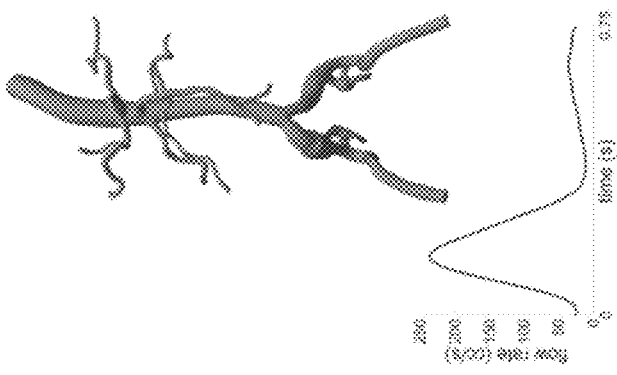
FIG. 10 illustrates a second example 1000 of an aorto-femoral model 1002 that may be used in connection with implementations of the disclosed technology and corresponding time-varying inflow waveform 1004.
Figure 9:
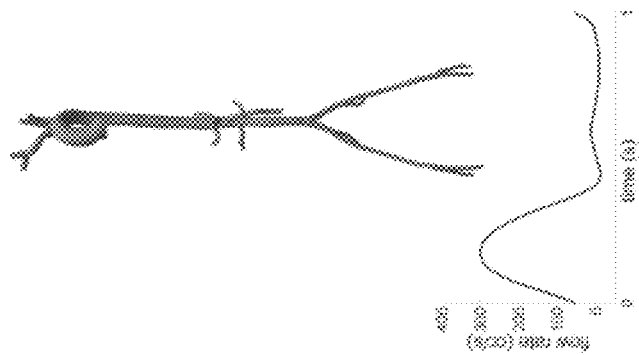
FIG. 9 illustrates a first example 900 of an aorto-femoral model 902 that may be used in connection with implementations of the disclosed technology and corresponding time-varying inflow waveform 904.

Implementations of the disclosed technology are generally directed to a distributed lumped parameter (DLP) modeling framework arranged to rapidly compute blood flow and pressure in vascular domains. This can be achieved by developing analytical expressions describing expected energy losses along vascular segments, including from viscous dissipation, unsteadiness, flow separation, vessel curvature and vessel bifurcations. This methodology can be applied to solve for unsteady blood flow and pressure in a variety of complex 3D image-based vascular geometries, which are typically approached using time-dependent computational fluid dynamics (CFD) simulations.

Implementations of the DLP framework disclosed herein generally demonstrate consistent agreement with CFD simulations for a range of flow conditions and vascular anatomies, with mean errors in flow rate and pressure less than 7% over the range models considered. The computational cost of the DLP framework is orders of magnitude lower than the computational cost of CFD, which opens new possibilities to use hemodynamics modeling for timely decision support in clinical settings, or to improve the ability to perform data assimilation, optimization, parameter tuning, uncertainty quantification and sensitivity analysis for cardiovascular modeling applications.

Implementations of the disclosed technology are generally directed to a distributed lumped parameter (DLP) framework to compute temporal flow and pressure in different vasculature models by taking into account various sources of energy dissipation. This approach results in ODEs that are significantly easier to solve than the aforementioned 1D and 2D PDE-based models. This approach can be even more accurate depending on the types of energy losses considered.

Most ROM approaches described above are reasonable in smaller vessels where the flow becomes 1D and fully developed. However, most ROMs produce erroneous results for flow in larger arteries, as typically derived from medical imaging, where flow conditions are known to be complex and unsteady.

Therefore, to evaluate the accuracy of the proposed DLP methodology, this framework is applied to a diverse range of healthy and diseased patient-specific cardiovascular anatomies including aortic, aorto-femoral, cerebrovascular, coronary, pulmonary and congenital heart disease models, and have compared the DLP results to the "gold-standard" from 3D time-dependent ("3Dt") CFD simulations. The ability of this framework to be automated provides many advantage for both exploratory and translational applications.

Similar to most fluid mechanic models, a relationship can be developed between flow and pressure from conservation of mass and balance of momentum principles. Namely, the formulation can be in terms of cross-sectionally averaged pressure P(x) and volumetric flow rate Q(x), where x denotes the axial coordinate along a given vessel. The cross-sectionally averaged Navier-Stokes equations, under suitable assumptions, reduce upon linearization to $$\frac{\partial A}{\partial t} + \frac{\partial Q}{\partial x} = 0 \quad (1)$$

$$\frac{\partial Q}{\partial t} + \frac{A_0}{\rho}\frac{\partial P}{\partial x} = f\frac{Q}{A_0}, \quad (2)$$

where $A_0$ is the reference cross-sectional area, $\rho$ is fluid density and f characterizes viscous dissipation. These equations have been widely used to describe flow and pressure in vascular domains, but are generally inaccurate in realistic geometries that contain energy loss due to curvature, flow separation, sudden expansions, etc. Therefore, as a basic adaptation, the dissipation term is redefined on the right hand side of Eq. (2) to account for losses neglected in deriving this equation. Namely, for a vascular segment of length L and (spatially varying) radius R, a momentum balance is considered of the form $$\left(\frac{\rho}{\pi}\int_0^L \frac{1}{R^2}dx\right)\frac{\partial Q}{\partial t} + \mathcal{R}Q + \Delta P = 0. \quad (3)$$

An appropriate vascular resistance can be defined by considering expected sources of energy dissipation, that when used in Eq. (3) and along with Eq. (1) and appropriate boundary conditions, provides accurate estimation of hemodynamics in realistic vascular geometries, particularly those derived from medical imaging and normally approached by CFD simulation.

Viscous Dissipation

Assuming Poiseuille flow, the pressure drop across a cylindrical vessel of length L is given by $\Delta P=R_v Q$, where $R_v=8\ \mu L/\pi R^4$ is the hydraulic resistance, with $\mu$ being the blood viscosity and R being the vessel radius. An integral form of this equation is considered to better account for potential variations of radius along the length of a vessel as $$R_v = \frac{8\mu}{\pi} \int_0^L \frac{1}{R(x)^3} dx \qquad (4)$$

For vessels of non-circular cross-section, $R(x)=\sqrt{A(x)/\pi}$ denotes the effective radius (henceforth radius) at local axial coordinate $x \in (0, L)$.

The Poiseuille law, $\Delta P=8\ \mu L Q/\pi R^4$, can be viewed a special case of the Darcy-Weisbach equation $$\Delta P = \lambda_s \frac{\rho}{2} \frac{V^2}{2R} \qquad (5)$$

where $V=Q/\pi R^2$ is the average fluid velocity, and $\lambda_s$ is the viscous friction factor. The viscous friction factor of a straight vessel is $\lambda_s=64/Re$, which yields Poiseuille's law, where Re denotes the Reynolds number. This viewpoint can be used next to incorporate pressure loss due to vessel curvature.

Curvature

The presence of centrifugal forces in a curved vessel results in a skewed velocity profile, which generally increases viscous dissipation as compared to flow through a straight vessel. Assuming steady and fully developed flow, the viscous friction factor of a curved vessel ($\lambda_c$) can be related to the viscous friction factor of a straight vessel ($\lambda_s$) with similar length and radius $$\gamma = \frac{\lambda_c}{\lambda_s} = 0.1033\sqrt{K}\left[\left(1+\frac{1.729}{K}\right)^{\frac{1}{2}} - \frac{1.315}{\sqrt{K}}\right]^{-3}, \qquad (6)$$

where $K=Re\sqrt{R/a}$ is the Dean number and a is the vessel curvature. Therefore, Eq. (4) can be modified to $$R_v = \frac{8\mu}{\pi}\int_0^L 0.1033\sqrt{K(x)}\left[\left(1+\frac{1.729}{K(x)}\right)^{\frac{1}{2}}-\frac{1.315}{\sqrt{K(x)}}\right]^{-2}\frac{1}{R(x)^4}dx \qquad (7)$$

Note that R, a and K generally vary as a function of x.

Expansions

The energy dissipation due to sudden expansions can be taken into account by using a semi-empirical model $$\Delta P = K_t \frac{\rho}{2 A_0^2}\left(\frac{A_0}{A_s}-1\right)^2 Q|Q|, \qquad (8)$$

where $A_s$ and $A_0$ are cross-sectional areas describing the expansion as described below, and $|Q|$ denotes the absolute value of flow rate (in case of reverse flow). Eq. (8) with $K_t=1$ can be derived from a control volume energy balance of inviscid flow through a sudden expansion. $K_t$ is added an empirical correction factor to account for losses from flow separation. A previous study showed that $K_t=1.52$ produced consistently accurate prediction of pressure drop compared to 3D simulations in realistic vascular (coronary) stenoses.

In this study, the local minima and maxima of R(x) were computed along each vessel segment. Then $A_s$ was computed at each local minimum. For each local minimum, $A_0$ was computed from the mean value of the radius at the local maxima immediately proximal and distal to the corresponding local minimum. For vascular segments with multiple sudden expansions, these losses were added in series $$R_s = \sum_{i=1}^n \frac{\rho K_t}{2 A_{0,i}^2}\left(\frac{A_{0,i}}{A_{s,i}}-1\right)^2 |Q|, \qquad (9)$$

where n is the number of sudden expansion locations over the given vascular segment. Aggregate losses due to sudden expansions were added in series to the viscous pressure loss derived above.

Bifurcations

Energy losses at vascular junctions were determined from geometric (branch angle) and hydraulic (flow split) considerations. Namely, the amount of pressure drop due to a vascular bifurcation was calculated as $$\Delta P = \frac{1}{2}\rho \frac{Q_{dat}^2}{A_{dat}^2}(1 + \lambda_j^2 \psi_j^2 - 2\lambda_j \psi_j \cos(\phi_j)), \qquad (10)$$

where $Q_{dat}$ and $A_{dat}$ are the flow rate and cross-sectional area of the datum supplier vessel, respectively. $\lambda_j=Q_j/Q_{dat}$ defines the volumetric flow split, $\psi_j=A_{dat}/A_j$ defines the area split and $\phi_j=3(\pi-\theta_j)/4$ is defined from the angle $\theta_j$ between a datum supplier and child branch. Hence the nonlinear resistance $$R_b = \frac{1}{2Q_j}\rho \frac{Q_{dat}^2}{A_{dat}^2}(1 + \lambda_j^2 \psi_j^2 - 2\lambda_j \psi_j \cos(\phi_j)) \qquad (11)$$

can be added in series to the resistances due to viscous and sudden expansion effects in the child branch.

Unsteadiness

Flow unsteadiness affects the momentum balance in Eq. (3) in two main ways. First, it explicitly leads to a change in fluid inertia as captured in the first term. Second, it implicitly changes the cross-sectional profile of the flow, which in turn changes the shear rate and viscous dissipation captured in the second term. To account for the later, the viscous resistance may be modified according to the Womersley number.

The Womersley number, $\alpha=R\sqrt{\rho\omega/\mu}$, quantifies the relative importance between pulsatile inertial effects and viscous effects. The heart rate is generally the dominant frequency and thus used to define $\omega$. For image-based vascular models, $\omega$, $\rho$ and $\mu$ vary minimally and thus intra- and inter-model variations of $\alpha$ are due to variations in vessel radius R.

As the Womersley number increases the velocity profile changes from parabolic to flat, increasing viscous losses. Based on the well-known Womersley's solution for pulsatile flow in a straight, rigid vessel, wall shear stress can be computed and then used to compute the (viscous) resistance due to Womersley flow. This can be used to define a function $\zeta(\alpha)$ describing the viscous resistance ratio between Womersley and Poiseuille flow. Hence, the (nominally Poiseuille) viscous resistance introduced in Eq. (4) can be modified to $$R_v = \frac{8\mu}{\pi} \int_0^L \zeta(\alpha(x)) \frac{1}{R(x)^4} dx, \quad (12)$$

where $\zeta$ is a function of x because R and hence $\alpha$ is a function of x. In this study, the maximum between curvature effect and pulsatile effect $\zeta$ was used in each artery to modify the Poiseuille resistance.

Implementation

Based on the above considerations, the resistance term in Eq. (3) can be given by $$R = \frac{8\mu}{\pi} \int_0^L \max(\gamma, \zeta) \frac{1}{R^4} dx + \sum_{i=1}^{n} \frac{\rho K_t}{2A_{0,i}^2} \left(\frac{A_{0,i}}{A_{s,i}} - 1\right)^2 |Q| + \frac{1}{2Q} \rho \frac{Q_{dat}^2}{A_{dat}^2} (1 + \lambda_j^2 \psi_j^2 - 2\lambda_j \psi_j - 2\lambda_j \varphi_j \cos(\phi_j)) \quad (13)$$

and Eq. (3) along with conservation of mass can be used to solve for flow rate through each vascular segment and pressure at vascular junctions.

Certain embodiments include an in-house Python framework to completely automate the DLP modeling procedure based on image-based geometry. Namely, the only input to the framework might be the geometric model (e.g. STL surface mesh) and specification of boundary conditions. Automated procedures can arranged to compute vessel lengths, bifurcation angles, and the variation of cross-sectional area and curvature along each vascular segment. A variety of boundary conditions can be implemented typical to current state-of-the-art image-based modeling, including specification of a time-varying flow or pressure waveform, or coupled LPN models at the inlet or outlets.

The end result is generally a system of nonlinear AEs and ODEs that describe the basic conservation laws and coupled boundary conditions. An implicit Euler scheme may be used to handle time-stepping. This results in a set of nonlinear algebraic equations to be solved each time-step, which is handled by iterative linearization. The solution of this system includes flow rate at all vascular segments and pressure values at all vascular junctions and boundaries.

In certain implementations, the DLP framework may be applied to a variety of image-based vascular models and the results were compared to those derived from CFD. An example included constructing a 3D model of the arteries from corresponding image data, employing and tuning boundary conditions representative of downstream and upstream physiology, finite element simulation of the 3D time-dependent Navier-Stokes equations, and post-processing to compute the flow rate and pressure at locations for comparison with the DLP model. All CFD simulations were run assuming rigid vessel walls. The domain was discretized using linear tetrahedral elements that included boundary layer meshing for all simulations. Mesh independence studies were undertaken for all 3D simulations to ensure that the results in the final meshes were not significantly affected by inadequate mesh resolution. Solutions were run until the pressure fields at the inlets and outlets did not change more than 1.0% compared to the solutions at the same time point in the previous cardiac cycle. Fluid properties (blood density $\rho=1.06$ g/cm$^3$ and blood viscosity $\rho=0.04$ dyn/(cm$^3$ s)) were assumed common among all models.

The DLP model is not tuned to the 3D CFD results. To ensure a consistent comparison, the same inlet and outlet boundary conditions were used. To quantify the comparison, the relative errors were calculated between the mean values of the temporal flow rate and pressure from the DLP model against those derived from CFD simulations at the inlets and outlets of each model. Values at the outlets were chosen because this evaluates the ability of the DLP model to serve as a surrogate for the entire 3D domain in applications such as UQ, parameter tuning, etc., and because these locations are generally where integrated differences become compounded (i.e., error is expected to accumulate as greater segments of vasculature is traversed). Nonetheless, the temporal variations in the flow rate and pressure computed from the DLP model were also compared with those from the 3D CFD simulations at several locations in the interior of the domain. For perspective, there was a comparison against results from a basic DLP model for which the Poiseuille resistance was assumed. This model can be viewed as the baseline model (cf. Eq. (2)) for which the corrections to the dissipation term proposed herein are neglected.

In the example, the DLP framework, on a single CPU core, took about 334±49 seconds to complete steps 102-110 of FIG. 1 over the range of models presented below.

Framework

FIG. 1 illustrates an example of modeling steps of a framework 100 for computing blood flow and pressure in a representative patient-specific coronary model using a distributed LP method in accordance with the disclosed technology. At 102, geometry of a vessel, e.g., an artery of a human subject is segmented in accordance with the techniques disclosed herein. At 104, one or more centerlines corresponding to portions of the vessel are generated. At 106, geometric features of the vessel are extracted. At 108, an LPN of resistors is constructed and, at 110, a system of equations are solved. At 112, postprocess simulation results are provided and may be provided as output, e.g., to a visual display, storage device, or both.

Aortic Models

Four aortic models 202, 302, 402, and 502 were considered including one normal, two coarctation (moderate and severe), and one aneurysmal, as illustrated by FIGS. 2-5, respectively. FIGS. 6 and 7 respectively illustrate relative errors of mean flow rates 600 and pressures 700 between the DLP model ($\overline{Q}_{0D}$, $\overline{P}_{0D}$) and CFD ($\overline{Q}_{3D}$, $\overline{P}_{3D}$) at the inlet and all outlets, demonstrating that the DLP model provides accurate prediction of mean flow rate and pressure in all cases when compared with CFD simulations. The mean value of the errors is less than 1% for all cases and the maximum error is ~1.5%. For comparison, when the baseline Poiseuille resistance is assigned to each vascular segment as illustrated by FIG. 8, the mean values of pressure ($\overline{P}_{pois}$) are significantly inaccurate, particularly for the cases with coarctation.

For all cases, phase-contrast (PC) MRI was used to measure flow in the ascending aorta. The respective volumetric flow waveforms from PC-MRI for each patient was mapped to the inlet of the CFD models using a time varying parabolic flow profile as the inflow boundary condition. Three-element "RCR" Windkessel models were coupled at all outlets. Regional mesh refinement was used for cases with aortic coarctation to resolve the complex flow features in the stenotic regions.

Aorto Femoral Models

Four aorto-femoral models 902, 1002, 1102, and 1202 were considered as illustrated by FIGS. 9-12. Model A (902) represents a non-diseased vasculature of significant spatial extent, which spanned from the aortic root to the femoral arteries. Model B (1002) had moderate aneurysms in both right and left common iliac arteries. Models C (1102) and D (1202) had relatively complex abdominal aortic aneurysms, with notable aortic curvature.

Figures 13, 14, 15:
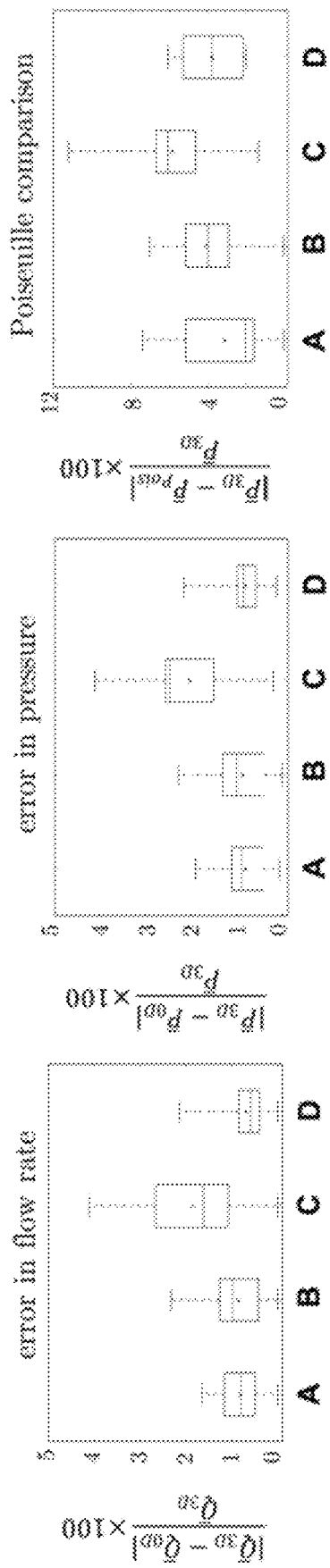
FIG. 13 illustrates an example 1300 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the aorto-femoral models 902, 1002, 1102, and 1202 of FIGS. 9-12, respectively.
FIG. 14 illustrates an example 1400 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the aorto-femoral models 902, 1002, 1102, and 1202 of FIGS. 9-12, respectively.
FIG. 15 illustrates an example 1500 of mean pressure errors between the 3Dt CFD and a DLP model assigning a Poiseuille resistance to each vascular segment ($\overline{P}_{pois}$), of the aorto-femoral models 902, 1002, 1102, and 1202 of FIGS. 9-12, respectively.

FIGS. 13 and 14 respectively illustrates the errors in mean flow rate 1300 and pressure 1400 between the DLP and CFD models, demonstrating that the results from the DLP model are in good agreement with CFD simulations. The mean value of the errors is less than 2% for all cases. A maximum error of 4% occurred at the right renal artery of Model C.

For Model A (902), an aortic flow waveform was adapted to have a mean cardiac output of 4.6 L/min (female). For Model B (1002) the supraceliac aorta blood flow waveform was derived from PC-MRI data. For Models C (1102) and D (1202) individualized inflow boundary conditions were determined based on the Baker equation, relating body surface area to cardiac output, and assuming that 70% of the cardiac output is distributed to the supraceliac aorta. The resulting mean flows were used to generate inflow waveforms by scaling a gender-matched representative supraceliac aortic flow waveform. Three element "RCR" Windkessel models were applied at each outlet. The values of the three parameters for each outlet are determined based on flow distributions to the outlets obtained from clinical PC-MRI measurements for Model B (1002), or from literature data for Models A (902), C (1102), and D (1202).

Coronary Models

Figures 21, 22, 23:
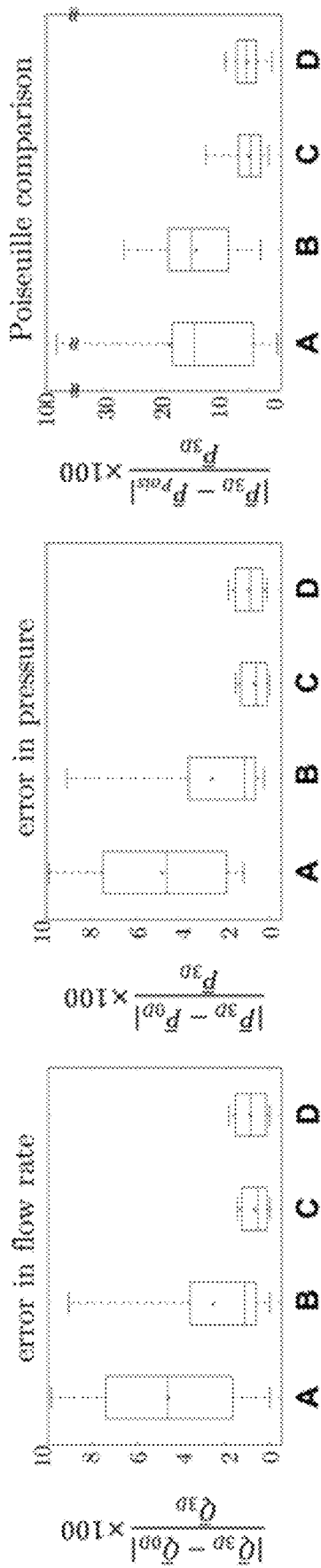
FIG. 21 illustrates an example 2100 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the coronary models of FIGS. 16-19.
FIG. 22 illustrates an example 2200 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the coronary models of FIGS. 16-19.
FIG. 23 illustrates an example 2300 of mean pressure errors between the 3Dt CFD and a DLP model assigning a Poiseuille resistance to each vascular segment ($\overline{P}_{pois}$), of the coronary models of FIGS. 16-19.
Figure 27:
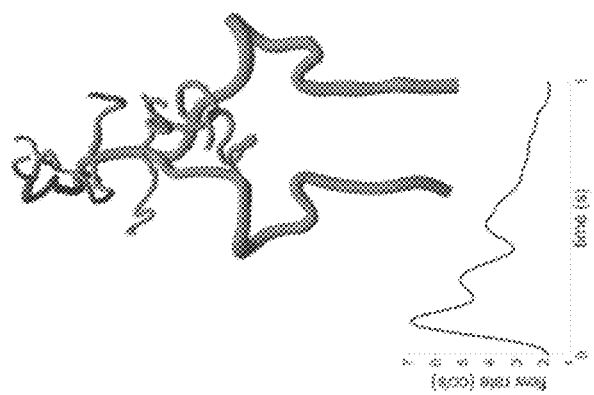
FIG. 27 illustrates a fourth example 2700 of a cerebrovascular model 2702 that may be used in connection with implementations of the disclosed technology and corresponding time-varying inflow waveform 2704 prescribed at the left and right vertebral arteries.
Figure 26:
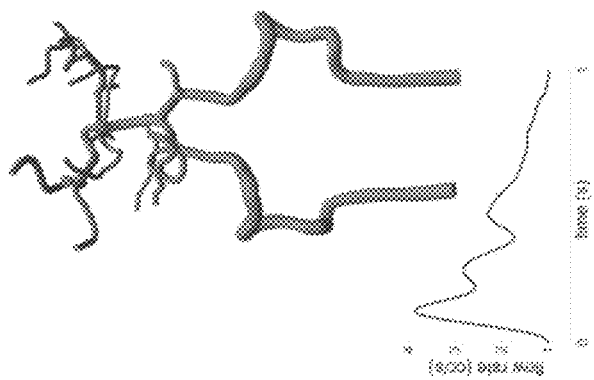
FIG. 26 illustrates a third example 2600 of a cerebrovascular model 2602 that may be used in connection with implementations of the disclosed technology and corresponding time-varying inflow waveform 2604 prescribed at the left and right vertebral arteries.
Figure 25:
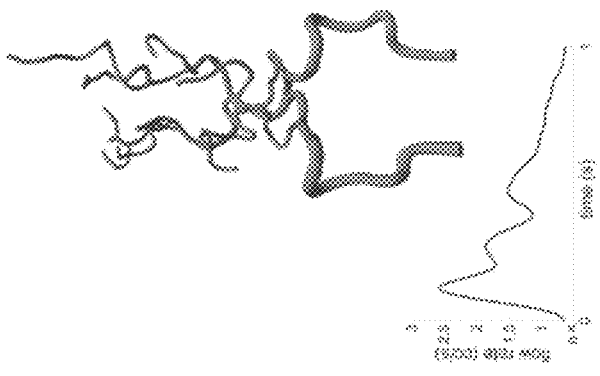
FIG. 25 illustrates a second example 2500 of a cerebrovascular model 2502 that may be used in connection with implementations of the disclosed technology and corresponding time-varying inflow waveform 2504 prescribed at the left and right vertebral arteries.
Figure 24:
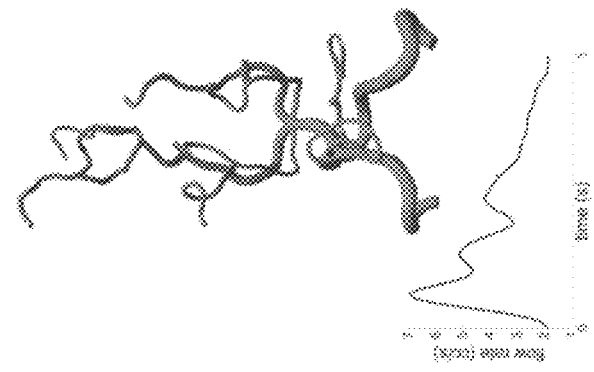
FIG. 24 illustrates a first example 2400 of a cerebrovascular model 2402 that may be used in connection with implementations of the disclosed technology and corresponding time-varying inflow waveform 2404 prescribed at the left and right vertebral arteries.

Four patient-specific models 1602, 1702, 1802, and 1902 of the proximal aorta and major coronary arteries were considered as illustrated by FIGS. 16-19, respectively. Model C (1802) represents a "healthy vasculature" with no observable coronary artery disease. Model B (1702) had a mild stenosis (~50%) in the mid left anterior descending (LAD) artery. Model D (1902) had ~50% diameter reduction in the right coronaries, at the bifurcation of the main and first marginal right coronary artery. Model A (1602) had a severe stenosis (~80%) in the first diagonal branch as well as a mild stenosis (~50%) in the beginning of the mid LAD. The mean value of the pressure errors were 5%, 2.6%, 0.7% and 0.9% for Models A (1602), B (1702), C (1802), and D (1902), respectively, as illustrated by FIG. 22. The maximum error of 10% was observed for one of the coronary branches of Model A (1602). This maximum error occurred in a healthy branch, and not in the complex stenotic region. For comparison, FIG. 23 illustrates corresponding errors from assigning the baseline Poiseuille resistance to each vascular segment, demonstrating significantly higher errors.

In all cases, aortic flow was prescribed at the inlet, an "RCR" Windkessel of the systemic circulation was coupled at the aortic outlet, and coronary-specific LPNs that consider the time-dependent intramyocardial pressure were coupled at the coronary outlets (each outlet having a separate such LPN). The effect of intramyocardial pressure is modeled by scaling the typical left and right ventricle pressures to recover realistic coronary flow waveforms. Namely, the left coronary waveform is described by low systolic flow and high diastolic flow, while the right coronary flow demonstrates two peaks one in systole and one in diastole. The LPN parameters of the systemic and coronary outlets were tuned to match target pressure and flow splits to the aorta and systemic and coronary outlets.

Cerebrovascular Models

Figure 28:
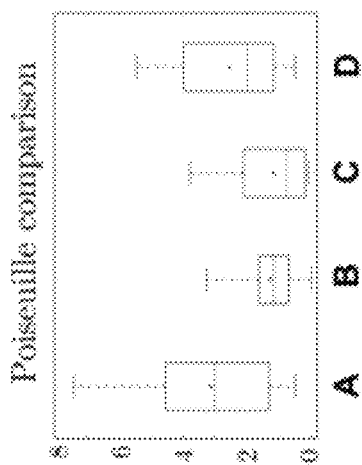
FIG. 28 illustrates an example 2800 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the cerebrovascular models 2402, 2502, 2602, and 2702 of FIGS. 24-27, respectively.
Figure 29:
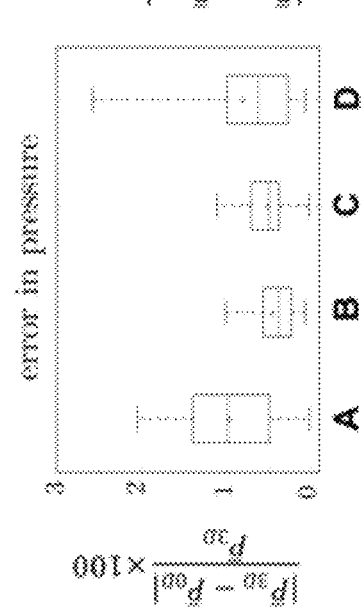
FIG. 29 illustrates an example 2900 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the cerebrovascular models 2402, 2502, 2602, and 2702 of FIGS. 24-27, respectively.
Figure 30:
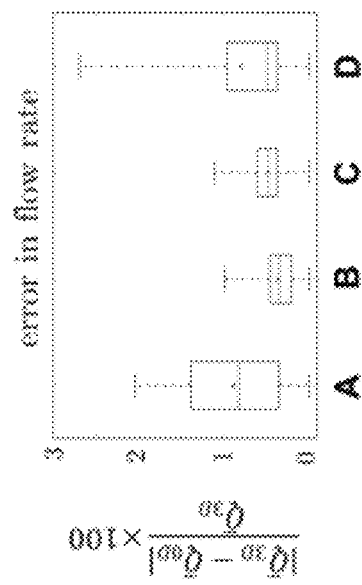
FIG. 30 illustrates an example 3000 of mean pressure errors between the 3Dt CFD and a DLP model assigning a Poiseuille resistance to each vascular segment ($\overline{P}_{pois}$), of the cerebrovascular models 2402, 2502, 2602, and 2702 of FIGS. 24-27, respectively.
Figures 31, 32, 33, 34:
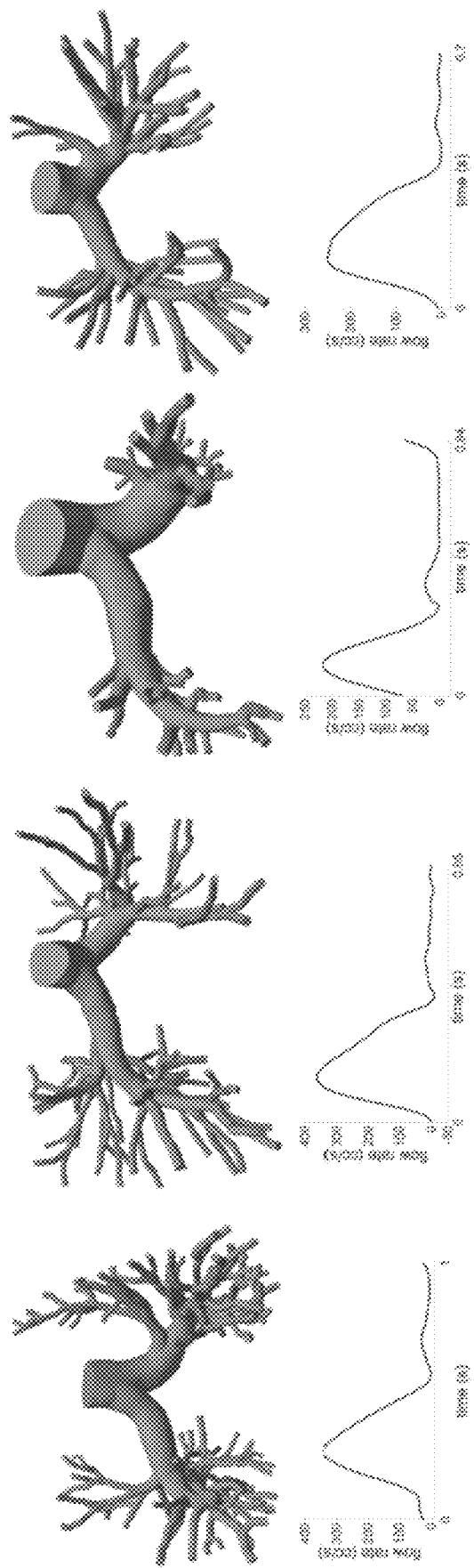
FIG. 31 illustrates a first example 3100 of a pulmonary model 3102 that may be used in connection with implementations of the disclosed technology and corresponding time-varying pulmonary blood flow waveform 3104.
FIG. 32 illustrates a second example 3200 of a pulmonary model 3202 that may be used in connection with implementations of the disclosed technology and corresponding time-varying pulmonary blood flow waveform 3204.
FIG. 33 illustrates a third example 3300 of a pulmonary model 3302 that may be used in connection with implementations of the disclosed technology and corresponding time-varying pulmonary blood flow waveform 3304.
FIG. 34 illustrates a fourth example 3400 of a pulmonary model 3402 that may be used in connection with implementations of the disclosed technology and corresponding time-varying pulmonary blood flow waveform 3404.

Four cerebrovascular models 2402, 2502, 2602, and 2702 were considered as illustrated by FIGS. 24-27, respectively. All of these models include the left and right vertebral arteries as inlets of the computational domain. The DLP model predicts consistently accurate flow rate and pressure results (FIGS. 28 and 29, respectively) with mean error values less than 1% for all cases. When Poiseuille resistance is used as illustrated by FIG. 30, the maximum errors are increased by a factor of greater than 3-fold when compared to our DLP model (right panel).

For all models, a characteristic vertebral blood flow waveform was scaled to match time-averaged PC-MRI measurements in the vertebral arteries and used to prescribe an inflow boundary condition to the computational models assuming a parabolic profile. Resistance boundary conditions were used at the outlets. A total resistance was calculated and distributed amongst the outlets by assuming all outlets act in parallel with values inversely proportional to the outlet area.

Pulmonary Models

Figures 35, 36, 37:
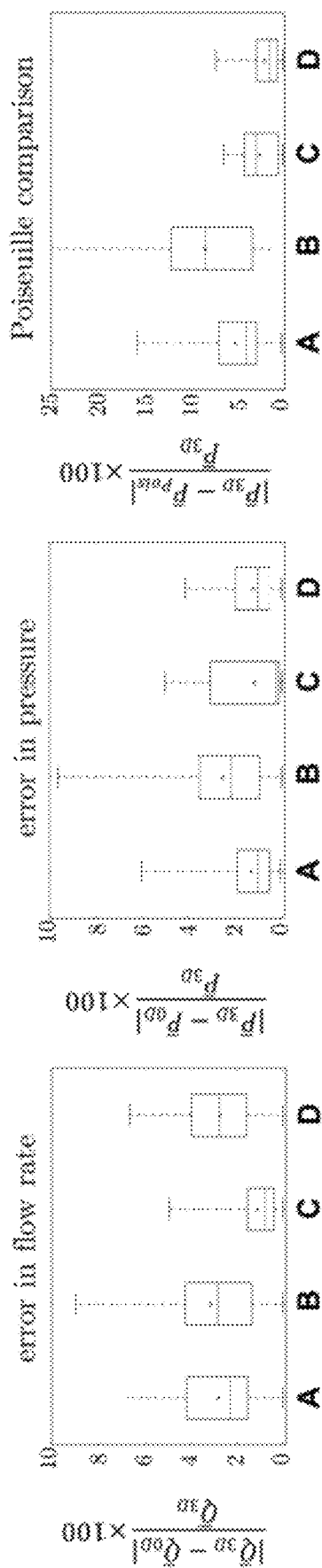
FIG. 35 illustrates an example 3500 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the pulmonary models 3102, 3202, 3302, and 3402 of FIGS. 31-34, respectively.
FIG. 36 illustrates an example 3600 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the pulmonary models 3102, 3202, 3302, and 3402 of FIGS. 31-34, respectively.
FIG. 37 illustrates an example 3700 of mean pressure errors between the 3Dt CFD and a DLP model assigning a Poiseuille resistance to each vascular segment ($\overline{P}_{pois}$), of the pulmonary models 3102, 3202, 3302, and 3402 of FIGS. 31-34, respectively.
Figure 41:
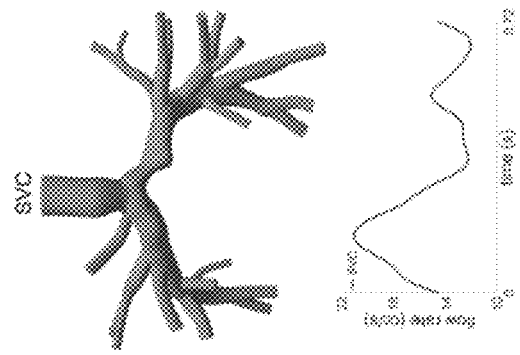
FIG. 41 illustrates a fourth example 4100 of a congenital heart disease model 4102 that may be used in connection with implementations of the disclosed technology and corresponding time-varying inflow waveform 4104 prescribed at the inlets.
Figure 40:
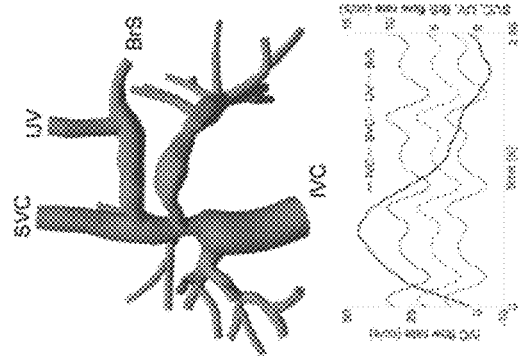
FIG. 40 illustrates a third example 4000 of a congenital heart disease model 4002 that may be used in connection with implementations of the disclosed technology and corresponding time-varying inflow waveform 4004 prescribed at the inlets.
Figure 39:
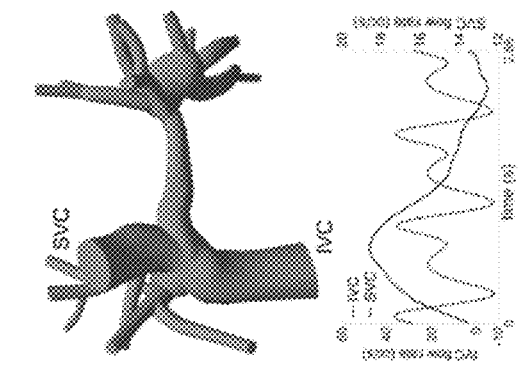
FIG. 39 illustrates a second example 3900 of a congenital heart disease model 3902 that may be used in connection with implementations of the disclosed technology and corresponding time-varying inflow waveform 3904 prescribed at the inlets.
Figure 38:
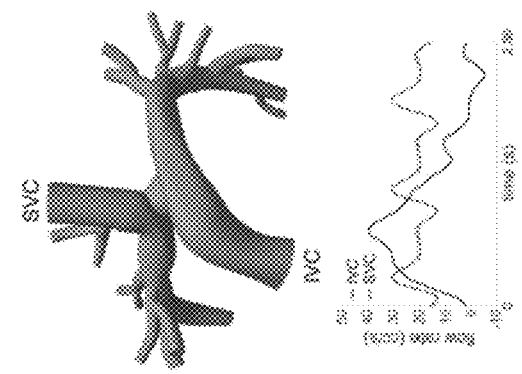
FIG. 38 illustrates a first example 3800 of a congenital heart disease model 3802 that may be used in connection with implementations of the disclosed technology and corresponding time-varying inflow waveform 3804 prescribed at the inlets.

Four patient-specific pulmonary models 3102, 3202, 3302, and 3402 extended from the main pulmonary artery to various levels of branching in the left and right pulmonary arteries (LPA, RPA) were considered as illustrated by FIGS. 31-34, respectively. FIG. 36 illustrates that the mean value of pressure errors is less than 3% for all pulmonary models tested. Simple Poiseuille model are relatively accurate Model C (3302) and D (3402), however, greater deviation is observed for Models A (3102) and B (3202) with more junctions. For example, the maximum pressure error increased from ~10% for our DLP model to ~25% for the baseline Poiseuille model.

Pulmonary blood flow waveforms 3104, 3204, 3304, and 3404 from PC-MRI are applied to the inlet of each model illustrated by FIGS. 31-34, respectively. The inflow waveforms were manipulated to have zero back flow to avoid numerical instability for 3D simulations. Resistance values were assigned at the outlet of each model based on the estimated mean pressure values of each patient, cross sectional area of the outlets, and left to right pulmonary flow split ratio that are obtained from PC-MRI data.

Congenital Heart Disease Models

Figures 42, 43, 44:
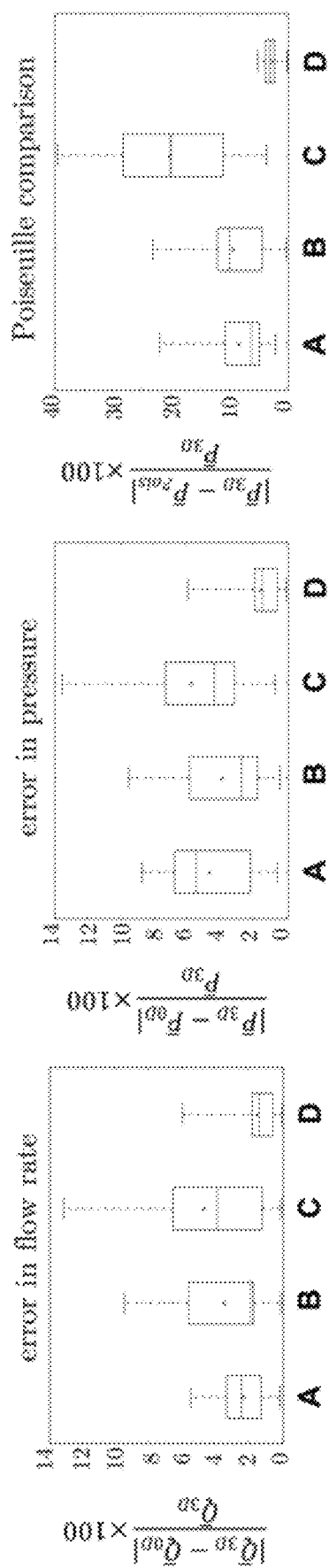
FIG. 42 illustrates an example 4200 of errors of mean flow rate between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the congenital heart disease models 3802, 3902, 4002, and 4102 of FIGS. 38-41, respectively.
FIG. 43 illustrates an example 4300 of errors of pressure between the DLP model ($\overline{Q}_{0D}$, $\overline{P}_{0D}$) and the full 3Dt CFD simulation ($\overline{Q}_{3D}$, $\overline{P}_{3D}$) at inlets and outlets of the congenital heart disease models 3802, 3902, 4002, and 4102 of FIGS. 38-41, respectively.
FIG. 44 illustrates an example 4400 of mean pressure errors between the 3Dt CFD and a DLP model assigning a Poiseuille resistance to each vascular segment ($\overline{P}_{pois}$), the congenital heart disease models 3802, 3902, 4002, and 4102 of FIGS. 38-41, respectively.

Models 3802, 3902, 4002, and 4102 from four pediatric patients with congenital heart disease were considered as illustrated by FIGS. 38-41, respectively. The DLP method maintained reliable agreement with 3D simulation results for blood flow simulations in models with congenital heart disease where the mean pressure errors are 4.7%, 3.9%, 5.8% and 1.6% for Models A (3802), B (3902), C (4002), and D (4102), respectively. The maximum error for all cases is <10% except for Model C (4002) that has the maximum error of 15%. As illustrated by FIG. 44, this maximum error significantly increased to ~40% when the baseline Poiseuille resistance is used. This also leads to higher mean errors of 5.8%, 7.0%, 20.2% and 2.8% for Models A (3802), B (3902), C (4002), and D (4102), respectively.

PC-MRI data was used to prescribe an inflow waveform to the inlets of computational domains. Inflow waveforms prescribed at the inferior and superior vena cava (IVC, SVC), internal jugular vein (IJV) and brachiocephalic vein (BrS) are shown in FIGS. 38-41 for all models. "RCR" boundary conditions were applied to each outlet. The "RCR" parameters are tuned to match the clinical target pressure values and assuming the LPA/RPA flow split ratio to be 45%/55% for all patients.

DISCUSSION

Implementations of the disclosed technology are generally directed to a DLP framework to predict temporal flow rate and pressure waveforms distributions in 3D image-based vascular models. The proposed DLP framework can provide consistent prediction with CFD simulations with mean errors <7% in a range of cardiovascular modeling applications. This framework can be fully automated based on an input model geometry (and specification of boundary conditions), and generally requires less than $\frac{1}{1000}$ of the computational cost of corresponding CFD simulations.

The instant disclosure includes the most comprehensive comparisons of a ROM to the current state-of-the-art image-based CFD modeling. A broad range of vascular anatomies and variations in geometric features were considered. Namely, the two key non-dimensional parameters of Reynolds (Re) and Womersley ($\alpha$) numbers varied from ~100-3,000 and ~1-20, respectively. Notably, these ranges in Re, $\alpha$, and vessel diameter span the spectrum of expected values encountered in most image-based computational modeling of blood flow. In addition to the dynamic and geometric difference explored, the number of vascular junctions across the models varied from 4 to 96. Interestingly, the junctions include both converging and diverging flows, where converging flows sometimes result in a negative loss coefficient, and in presence of back flow, some bifurcations can have both diverging and converging flows at different time points of the cardiac cycle. Additionally, vascular expansions, as quantified by the area reduction ratio $A_s/A_0$, ranged up to ~90%, and the mean curvature ratio $\delta = a/R$ ranged up to ~0.5 in the considered models, which again cover a broad range of expected values.

To provide more general insight into the contribution of each source of energy dissipation, the modification due to flow separation downstream of expansions, when present, may have the highest contribution to accurately predict flow and pressure in the corresponding model. Viscous dissipation introduced by curvature effects generally has the second highest contribution in energy losses. This can be confirmed by comparing the second and third panels of error plots for coronary models with negligible unsteadiness effect, particularly for the healthy coronary Model C or Models B and D with mild stenoses.

Moreover, for cerebrovascular models the results are improved mostly by considering the curvature effects, since the Womersley number is ≈2 in these models and there is no sudden changes in cross-sectional area. The Womersley effect has the next highest impact on modifying Poiseuille resistance model, where viscous resistance can increase by a factor of 5 in for example aortic branches. The Womersley effect can be seen for example in the aorto-femoral models where the errors approximately tripled without considering this effect. Finally, the energetic losses due to bifurcations was found to be relatively negligible, except in cases where numerous junctions exist, such as pulmonary models.

Given the accuracy of the DLP approach, implementations of the disclosed technology can potentially replace CFD in applications where time is of the essence, thus opening the door to broader use of image-based modeling in, for example, clinical settings. A major impact of this approach is to applications where numerous CFD simulations would be desirable, such as for model parameter or boundary condition tuning, uncertainty quantification, sensitivity analysis, surgery/device design, data assimilation, machine learning training, etc. In such scenarios, it could be the de facto model, or used in conjunction with more expensive CFD simulations to reduce the number of full CFD model evaluations. This could be highly significant as the above types of engineering analyses are playing an increasing role in image-based modeling research and translational applications.

The following discussion is intended to provide a brief, general description of a suitable machine in which embodiments of the disclosed technology can be implemented. As used herein, the term "machine" is intended to broadly encompass a single machine or a system of communicatively coupled machines or devices operating together. Exemplary machines may include computing devices such as personal computers, workstations, servers, portable computers, handheld devices, tablet devices, and the like.

Typically, a machine includes a system bus to which processors, memory such as random access memory (RAM), read-only memory (ROM), and other state-preserving medium, storage devices, a video interface, and input/output interface ports can be attached. The machine may also include embedded controllers such as programmable or non-programmable logic devices or arrays, Application Specific Integrated Circuits (ASICs), embedded computers, smart cards, and the like. The machine may be controlled, at least in part, by input from conventional input devices such as keyboards and mice, as well as by directives received from another machine, interaction with a virtual reality (VR) environment, biometric feedback, or other pertinent input.

The machine may utilize one or more connections to one or more remote machines, such as through a network interface, modem, or other communicative coupling. Machines can be interconnected by way of a physical and/or logical network, such as an intranet, the Internet, local area networks, wide area networks, etc. One having ordinary skill in the art will appreciate that network communication may utilize various wired and/or wireless short range or long range carriers and protocols, including radio frequency (RF), satellite, microwave, Institute of Electrical and Electronics Engineers (IEEE) 545.11, Bluetooth, optical, infrared, cable, laser, etc.

Embodiments of the disclosed technology may be described by reference to or in conjunction with associated data including functions, procedures, data structures, application programs, instructions, etc. that, when accessed by a machine, may result in the machine performing tasks or defining abstract data types or low-level hardware contexts. Associated data may be stored in, for example, volatile and/or non-volatile memory, such as RAM and ROM, or in other storage devices and their associated storage media, which can include hard-drives, floppy-disks, optical storage, tapes, flash memory, memory sticks, digital video disks, biological storage, and other non-transitory, physical storage media.

Associated data may be delivered over transmission environments, including the physical and/or logical network, in the form of packets, serial data, parallel data, etc., and may be used in a compressed or encrypted format. Associated data may be used in a distributed environment, and stored locally and/or remotely for machine access.

Having described and illustrated the principles of the invention with reference to illustrated embodiments, it will be recognized that the illustrated embodiments may be modified in arrangement and detail without departing from such principles, and may be combined in any desired manner And although the foregoing discussion has focused on particular embodiments, other configurations are contemplated.

Consequently, in view of the wide variety of permutations to the embodiments that are described herein, this detailed description and accompanying material is intended to be illustrative only, and should not be taken as limiting the scope of the invention. What is claimed as the invention, therefore, is all such modifications as may come within the scope and spirit of the following claims and equivalents thereto.

We claim:

1. A computer-implemented method for non-invasive assessment of a patient's hemodynamics information, comprising:
generating, based on image data of the patient, a geometric model of at least one portion of a cardiovascular system of the patient;
determining, from the geometric model, one or more geometric features, the one or more geometric features including vessel length, one or more bifurcation angles, variation of cross-sectional area, and/or curvature along each of one or more vascular segments of the at least one portion of the cardiovascular system;
constructing a lumped parameter network (LPN) of resistors corresponding to the at least one portion of the cardiovascular system based on the one or more geometric features, wherein the LPN of resistors defines expected energy losses along the one or more vascular segments from viscous dissipation, unsteadiness, flow separation, vessel curvature, and/or vessel bifurcation; and
solving a system of equations corresponding to flow and pressure for the LPN in order to calculate a flow rate through each of the one or more vascular segments and pressure at one or more vascular junctions of the at least one portion of the cardiovascular system.

2. The computer-implemented method of claim 1, further comprising providing a 3D representation corresponding to a result of the solving.

3. The computer-implemented method of claim 1, wherein the one or more geometric features includes the vessel length and further includes vessel radius, and wherein the LPN of resistors defines expected energy losses along the one or more vascular segments from viscous dissipation based on the vessel length and the vessel radius.

4. The computer-implemented method of claim 3, wherein the viscous dissipation is further based on the vessel curvature.

5. The computer-implemented method of claim 3, wherein the viscous dissipation is modified based on a Womersley number to account for flow unsteadiness, the Womersley number determined based on variation of the vessel radius.

6. The computer-implemented method of claim 1, wherein the one or more geometric features includes the one or more bifurcation angles, and wherein the LPN of resistors defines expected energy losses along the one or more vascular segments from a vessel bifurcation based on a flow rate and cross-sectional area of a supplier vessel and a bifurcation angle of the one or more bifurcation angles.

7. The computer-implemented method of claim 1, wherein the one or more geometric features includes the variation of cross-sectional area, and wherein the LPN of resistors defines expected energy losses along the one or more vascular segments from flow separation downstream of expansions based on the variation of cross-sectional area.

8. The computer-implemented method of claim 1, wherein the geometric model is a surface mesh model and wherein the LPN is not tuned to computational fluid dynamics (CFD) results.

9. The computer-implemented method of claim 1, wherein solving the system of equations corresponding to flow and pressure for the LPN includes solving the system of equations for the LPN and one or more boundary conditions.

10. The computer-implemented method of claim 1, wherein the one or more geometric features includes a vascular obstruction.

11. The computer-implemented method of claim 9, wherein the one or more boundary conditions include a time-varying flow or pressure waveform.

12. The computer-implemented method of claim 9, wherein the portion of the cardiovascular system includes the proximal aorta and major coronary arteries, and wherein the one or more boundary conditions include an aortic flow rate, an RCR Windkessel of systemic circulation, and a plurality of coronary-specific LPNs.

13. The computer-implemented method of claim 1, wherein the LPN describes a mathematical relationship between blood flow, blood pressure, and their derivatives.

14. The computer-implemented method of claim 1, wherein blood flow rate is linearly proportional to pressure drop across the network in the LPN.

15. One or more tangible, non-transitory computer-readable media storing instructions that, when executed by a processor, cause the processor to perform the computer-implemented method of claim 1.

16. A computer-implemented method, comprising:
predicting temporal blood flow and pressure of a portion of a cardiovascular system of a patient based on output from a distributed lumped parameter (DLP) framework, the output from the DLP framework generated based on a 3D model of the portion of the cardiovascular system of the patient generated from image data of the patient, the DLP framework configured to extract one or more geometric features from the 3D model and calculate, based on the one or more geometric features and input boundary conditions, expected energy losses along the one or more vascular segments from viscous dissipation, unsteadiness, expansions, vessel curvature, and/or vessel bifurcation.

17. The computer-implemented method of claim 16, wherein the DLP framework is configured to calculate expected energy losses along the one or more vascular segments from viscous dissipation along the one or vascular segments, one or more expansions in the one or more vascular segments, and one or more vessel bifurcations in the one or more vascular segments.

18. The computer-implemented method of claim 16, wherein the DLP framework is configured to calculate expected energy losses along the one or more vascular segments based on a maximum between a curvature effect and a pulsatile effect used to modify an initial viscous dissipation along the one or more vascular segments.

* * * * *